United States Patent [19]

Lippsmeier et al.

[11] 4,028,421
[45] * June 7, 1977

[54] PRODUCTION OF TERTIARY (HYDROXYMETHYL)-METHYLPHOSPHINE OXIDES

[75] Inventors: Bernd Lippsmeier, Hurth-Knapsack; Klaus Hestermann, Erftstadt Bliesheim; Martin Reuter, Frankfurt am Main-Unterliederbach, all of Germany

[73] Assignee: Hoechst Aktiengesellschaft, Frankfurt am Main, Germany

[ * ] Notice: The portion of the term of this patent subsequent to Apr. 26, 1994, has been disclaimed.

[22] Filed: Mar. 21, 1975

[21] Appl. No.: 560,890

[30] Foreign Application Priority Data

Mar. 22, 1974 Germany ............... 2413824

[52] U.S. Cl. .................................. 260/606.5 P
[51] Int. Cl.² ...................................... C07F 9/53
[58] Field of Search ........................ 260/606.5 P

[56] References Cited

UNITED STATES PATENTS

| 3,030,421 | 4/1962 | Reuter et al. | 260/606.5 P |
| 3,660,495 | 5/1972 | Chingtsung Lin | 260/606.5 P |
| 3,732,316 | 5/1973 | Chingtsung Lin | 260/606.5 P |
| 3,928,463 | 12/1975 | Reuter | 260/606.5 P |

OTHER PUBLICATIONS

Chemical Abstracts, 68, 87350$q$ (1968).
Chemical Abstracts, 70, 115227$s$ (1969).
Hellmann et al., Ann. V659, pp. 49–63 (1962).
Epstein et al., Tetrahedron, V18 pp. 1231–1242 (1962).
Buckler et al., Tetrahedron, V18 pp. 1211–1219 (1962).
Trippett, J. Chem. Soc. pp. 2813–2816 (1961).
Buckler, J.A.C.S. V82, pp. 4215–4220 (1960).
Buckler et al., J.A.C.S. V82, pp. 2076–2077 (1960).

Primary Examiner—Helen M. S. Sneed
Attorney, Agent, or Firm—Connolly and Hutz

[57] ABSTRACT

Production of tertiary (hydroxymethyl)-methylphosphine oxides of the general formula:

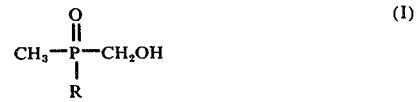

in which R stands for a branched or unbranched, substituted or unsubstituted alkyl, cycloalkyl, aralkyl or aryl group having from 1 to 18 carbon atoms. To this end tertiary bis-(hydroxymethyl)-phosphines of the general formula

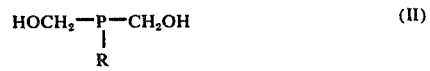

in which R has the meaning given above, are subjected to a thermal rearrangement reaction at temperatures higher than about 90° C or at temperatures within the range −10° and +250° C, in the presence of a catalyst.

3 Claims, No Drawings

PRODUCTION OF TERTIARY (HYDROXYMETHYL)-METHYLPHOSPHINE OXIDES

The present invention relates to a process for making tertiary (hydroxymethyl)-methylphosphine oxides of the general formula:

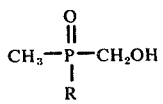

in which R stands for a branched or unbranched, substituted or unsubstituted alkyl, cycloalkyl, aralkyl or aryl group other than a hydroxymethyl group, having from 1 to 18, preferably from 1 to 6, more preferably from 1 to 2, carbon atoms, the useful substituents being selected from those which are inert under the reaction conditions.

The above process is more particularly used for making (hydroxymethyl)-dimethylphosphine oxide.

It is known that (hydroxymethyl)-alkyl (or aryl)-phosphine oxides can be made by oxidizing (hydroxymethyl)-alkyl (or aryl)-phosphines with an oxidant (e.g. $H_2O_2$), in known manner. The particular tertiary (hydroxymethyl)-phosphines can be made by subjecting the corresponding phosphonium salts to a cleavage reaction in an alkaline medium.

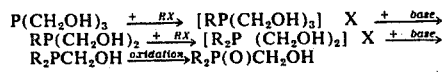

In the above equations, R stands for alkyl, cycloalkyl or aryl, X stands for chlorine, bromine or iodine and the base is triethylamine. (R. K. Valetdinov, E. V. Kuznetzov, R. R. Betova, R. K. Mukhaeva, Zh. Obshch. Khim. 37 (10), 2269 (1967); H. Hellmann, J. Bader, H. Birkner and O. Schumacher, Liebigs Annalen, volume 659, 49 (1962)).

Very moderate yields are obtained, especially in those cases in which (hydroxymethyl)-methylphosphonium salts are subjected to an alkaline decomposition with tertiary amines, which calls for considerable expenditure of energy and chemicals. In addition to this, formaldehyde is obtained as a by-product which is very difficult to separate.

A further process has been described, wherein (hydroxymethyl)-dimethylphosphine oxide is produced via the dimethylphosphine oxide stage

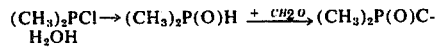

and wherein it is necessary for the dimethylchlorophosphine or dimethylphosphine oxide starting material to be prepared in costly and difficult manner. (F. Seel, K. H. Rudolph and W. Gombler, Angew. Chemie 79, 686 (1967); H. Staendeke, H. J. Kleiner, Angew. Chemie 85, 973 (1973); M. Fild and R. Schmutzler, G. M. Kosolapoff and L. Maier, "Organic Phosphorus Compounds", vol. 4, Wiley-Interscience, New York (1972), pages 75 et seq; German published Specifications "Offenlegungsschriften" Nos. 1,568,928 and 1,618,603).

A still further process for making methylphosphines has been described in U.S. Pat. No. 3,732,316, wherein a hydroxymethylphosphine in an inert polar solvent is heated for as long as necessary at temperatures at which it is isomerized to methylphosphine oxide. Specifically described therein is only the preparation of bis-(hydroxymethyl)-methylphosphine oxide by subjecting tris-(hydroxymethyl)-phosphine to a rearrangement reaction.

In accordance with the present invention, we have now unexpectedly found that it is also possible for tertiary bis-(hydroxymethyl)-phosphines (II) to be transformed to tertiary (hydroxymethyl)-methylphosphine oxides (I) if advantage is taken of the so-called "Buckler-Tripett rearrangement reaction", which is known for some time to describe the isomerization of tertiary phosphines containing α-hydroxyl groups (H. Hellmann, J. Bader, H. Birkner and O. Schumacher, Liebigs Annalen, vol. 659, 49 et seq. (1962), Houben-Weyl "Methoden der Organischen Chemie", Georg Thieme Verlag Stuttgart (1963), volume XII/1, page 30).

The present invention relates more particularly to a process for making tertiary (hydroxymethyl)-methylphosphine oxides of the general formula:

in which R stands for branched or linear, substituted or unsubstituted alkyl, cycloalkyl, aralkyl or aryl groups other than a hydroxymethyl group, having from 1 to 18, preferably from 1 to 6, more preferably from 1 to 2, carbon atoms, the substituents of those groups being inert under the reaction conditions, which process comprises subjecting tertiary bis-(hydroxymethyl)-phosphines of the general formula:

in which R has the meanings given above, to a thermal rearrangement reaction at temperatures higher than about 90° C or, in the presence of a catalyst, at temperatures within the range −10° and +250° C.

It is possible for the above rearrangement reaction to be effected in the presence of inert, e.g. polar organic solvents or dispersants, such as alcohols, glycols, formamides, aliphatic or aromatic nitriles, ethers, halogenated aliphatic or aromatic hydrocarbons, alkylated urea derivatives cyclic or linear sulfones, carboxylic acid esters, anhydrides or amides, sulfoxides or blends thereof. The rearrangement reaction should more preferably be effected in the presence of dimethylformamide, benzonitrile, propionitrile, dioxane, o-dichlorobenzene, sulfolane, N-methylpyrrolidone, dimethylsulfoxide or (hydroxymethyl)-methylphosphine oxide of general formula (I), the latter being prefabricated in each particular case.

It is even more preferable for the rearrangement reaction to be carried out in the presence of unpolar solvents or dispersants. In this latter case, it is particularly advantageous to use unbranched or branched aliphatic or cycloaliphatic or aromatic hydrocarbons, such as petroleum ether, octane, dodecane or decaline.

The thermal treatment should conveniently be effected at temperatures within the range 90° and 180° C. In those cases in which the rearrangement is effected in the presence of catalysts, it is good practice to use a Lewis acid catalyst, e.g. $BF_3$.etherate. The catalyst should preferably be used in a proportion of at least 1 weight %. If carried out in the presence of catalysts, it is most preferable for the rearrangement reaction to be carried out at temperatures within the range $-10°$ and $+180°$ C.

It is also possible for the rearrangement reaction to be carried out in the absence of solvents or dispersants. In this case, it is advantageous for it to be effected in a thin layer evaporator, tubular reactor or packed column, especially in a column packed with metal powder, quartz sand, glass rings or balls, at temperatures within the range $130°$ and $250°$ C.

The use of an unpolar solvent or dispersant has the technically beneficial effect that the resulting reaction product does generally not mix with the diluent used in each particular case and that the desirable phosphine oxide is easy to separate by phase separation. In some cases, it is possible for dissolved contaminants or by-products to be retained in the second phase, which means an additional purification effect.

If the hydroxymethylphosphines used have a sufficient thermal stability, it is possible for the solvent to be completely omitted in carrying out the rearrangement reaction which, however, sould then be effected within periods as short as possible.

A particularly preferred embodiment of the present process comprises making (hydroxymethyl)-dimethylphosphine oxide from primary methylphosphine. To this end, the primary methylphosphine is reacted at atmospheric pressure at temperatures lower than $40°$ C, preferably within the range $30°$ and $35°$ C, with formaldehyde, paraformaldehyde or trioxane in the presence of polar organic solvents being inert with respect to the reactants and the resulting reaction product. The resulting bis(hydroxymethyl)-methylphosphine is left unseparated and subjected to a thermal rearrangement reaction at temperatures higher than about $90°$ C, preferably within the range $90°$ and $250°$ C, more preferably within the range $90°$ and $180°$ C, or admixed with a catalyst and then treated at temperatures within the range $-10°$ and $+250°$ C.

The polar solvents used in the embodiment just described should conveniently be selected from alcohols, glycols, alkylated formamides, aliphatic or aromatic nitriles, ethers, halogenated aliphatic or aromatic hydrocarbons, alkylated urea derivatives, cyclic or linear sulfones, carboxylic acid esters, anhydrides or amides, sulfoxides or blends thereof. Particularly useful are dimethylformamide, benzonitrile, propionitrile, dioxane, o-dichlorobenzene, sulfolane, N-methylpyrrolidone or dimethylsulfoxide, especially in admixture with lower alcohols, such as methanol and ethanol. If the rearrangement reaction is effected in the presence of catalysts, it is good practice for the catalysts to be selected from carbon tetrachloride or tetrabromide or Lewis acids, e.g. $BF_3$ . etherate. The catalysts should preferably be used in proportions of at least 1 weight % and the reaction should be effected at temperatures within the range $-10°$ and $+180°$ C.

The reaction periods are within the range about 2 and 60 hours.

It is also advantageous for the reaction to be carried out under inert gas, e.g. nitrogen, carbon dioxide or argon.

(Hydroxymethyl)-methylphosphine oxides are interesting flameproofing agents. They can also be used as intermediates in making other flameproofing agents, plant protecting agents and pharmaceutical preparations.

EXAMPLE 1

50 g of bis-(hydroxymethyl)-methylphosphine was added dropwise with agitation, within 50 minutes at $130°$ C and under nitrogen to 130 g of benzonitrile, and the whole was heated for a further 4 hours to $130°$ C. After cooling, a clear solution was obtained which was distilled under vacuum and thereby freed from the solvent. 48.9 g of a crystalline rearrangement product melting at $65°-70°$ C remained behind. The product was subjected to NMR-spectroscopy and gas chromatography and found to contain 82% of (hydroxymethyl)-dimethylphosphine oxide. ($^{31}$P-NMR: $-53$ ppm; compared with standard $H_3PO_4$ of 85% strength). Titration with iodine indicated that the product was practically free from trivalent phosphorus compounds.

The product could be further purified by fractional distillation under vacuum ($bp_{0.2}$ mm Hg: $138°-140°$ C) or by recrystallization from methylene chloride (mp: $74°-76°$ C). In its chemical, physical and spectroscopic properties (IR and NMR), the product so made was found to be identical with a comparative product prepared from tris-(hydroxymethyl)-phosphine and methyl iodide by multiple stage alkaline degradation (R. K. Vateldinov et al. Zh. Obshch, Khim 37, (10) 2269 (1967)).

Analysis: $C_3H_9O_2P$. Calculated: C, 33.3; H, 8.4; P, 28.7%. Found: C, 33.5; H, 8.7; P, 28.5%.

EXAMPLES 2, 3 and 4

The procedure was the same as that described in Example 1 save that the benzonitrile was replaced once by dimethylsulfoxide, once by N-methylpyrrolidone and once by dimethylformamide. Results similar to those in Example 1 were obtained at the boiling temperature of these compounds. The reaction periods were within the range 4 and 8 hours.

EXAMPLE 5

100 g of o-dichlorobenzene was heated to $180°$ C under nitrogen. 54 g of bis-(hydroxymethyl)-methylphosphine was added dropwise within 15 minutes and the whole was thoroughly mixed. Following this, the whole was stirred for a further 6 hours at $180°$ C under reflux. After cooling, there were obtained two phases which were separated from each other in known manner, in a funnel separator. The upper phase contained (hydroxymethyl)dimethylphosphine oxide as desirable rearrangement product. The product was treated under vacuum to remove solvent residues, if any. 52 g of a colorless viscous oil which crystallized on being allowed to stand (mp: $65°-70°$ C) was obtained. The product was identical with that obtained in Example 1. It contained 78.2% of $(CH_3)_2P(O)CH_2OH$. A minor quantity of desirable final product was obtained by distillative work-up of the lower solvent phase. The product can be further purified by subjecting it to the treatment described in Example 1.

The same result as that described hereinabove is obtained by replacing the o-dichlorobenzene by octane, decaline or toluene. The compounds were used at their respective boiling temperature. The reaction periods were within the range 8 and 20 hours and the yields were within the range 76 and 83% of the theoretical.

EXAMPLE 6

20 cc of o-dichlorobenzene was admixed dropwise with very careful exclusion of oxygen (stream of argon), with agitation, at 160° C and within 30 minutes, with a mixture of 15 g of o-dichlorobenzene and 15 g (0.1 mol) of bis-(hydroxymethyl)-n-butylphosphine. Following this, the whole was heated for altogether 12 hours to reflux temperature. The o-dichlorobenzene was removed under vacuum (70° C at 1 mm Hg) and 14.8 g of a colorless highly viscous oil was obtained. The oil could not be found to crystallize even after having been allowed to stand for some prolonged time. Titration with iodine showed that the product was free from trivalent phosphorus compounds. NMR-spectroscopy indicated that the product contained 76.2% of (hydroxmethyl)-n-butyl-methylphosphine oxide ($^{31}$P-NMR: −52 ppm, determined in CDCl$_3$ with standard H$_3$PO$_4$ of 85% strength). The product could be further purified by known methods.

EXAMPLE 7

54 g of bis-(hydroxymethyl)-methylphosphine was so supplied under nitrogen at 250° C to a thin layer evaporator that the total reaction period was 4 hours. 52 g of a colorless oil which solidified gradually on cooling was obtained. NMR-spectroscopy and iodometric titration indicated a 84% rearrangement of the phosphine used. By recrystallization or distillation in vacuum, it was possible to obtain crystalline (hydroxymethyl)-dimethylphosphine oxide (mp: 74°–77° C).

EXAMPLE 8

100 ml of benzonitrile containing 2.5 weight % of BF$_3$ . etherate was added dropwise, within 2 hours, at 125° C, under nitrogen and with thorough agitation to a solution of 54 g (0.5 mol) of bis-(hydroxymethyl)methylphosphine in 100 ml of benzonitrile. Following this, the whole was heated for a further 1–2 hours to reflux temperature and the solvent was removed by distillation under vacuum. The residue was a slightly yellowish viscous oil of which 79.8% was hydroxymethyl-dimetylphosphine oxide. The product was purified as described and found to be identical with that obtained in Example 1.

EXAMPLE 9

30 g (1 mol) of paraformaldehyde was suspended in a mixture of 10 ml of methanol and 25 ml of benzonitrile under nitrogen in a 100 ml round flask provided with gas inlet, stirrer, reflux condenser and fractionating column. The whole was thoroughly mixed and methylphosphine was introduced thereinto until a clear solution was obtained. The reaction temperature was at most 40° C. Following this, the reaction temperature was increased gradually to 130° C. The cooling liquid in the reflux condenser had a temperature of 65°–70° C which made it possible for the alcohol to distil off. Once the desirable reaction temperature was reached, the reaction mixture was stirred for altogether a further 8 hours at 130° C. The solvent was removed by distillation under vacuum and 53.2 g of a slightly yellowish highly viscous residue, which crystallized gradually on standing, was obtained. NMR-spectroscopy indicated that it contained 74.8% of (hydroxymethyl)-dimethylphosphine oxide. The product could be further purified in known manner, e.g. by distillation or recrystallization.

EXAMPLE 10

The procedure was the same as that described in Example 9 save that 1.5 g of BF$_3$ . etherate was added, once the desirable reaction temperature was reached. The reaction was complete after as short a period as 6 hours. This was easy to identify by titration with iodine in an acid medium. The crude (hydroxymethyl)-dimethylphosphine oxide so obtained was worked up and purified in the manner described hereinabove.

We claim:

1. In the process for making tertiary methylphosphine oxides of the formula

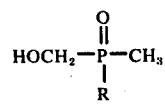

in which R is identical or different alkyls other than hydroxymethyl having 1 to 6 carbon atoms by rearranging tertiary bis-(hydroxymethyl)-phosphines of the formula

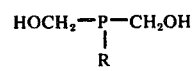

in which R has the meanings given above, in the presence of a catalyst and in the absence of oxygen, water and alcohol at minus 10° to plus 250° C, the improvement which comprises using BF$_3$ . etherate as catalyst.

2. The process of claim 1 wherein R has 1 or 2 carbon atoms.

3. The process of claim 1, wherein the rearrangement of the tertiary hydroxymethyl-phosphines is effected in a thin layer evaporator, tubular reactor or packed column.

* * * * *